(12) United States Patent
Domaille et al.

(10) Patent No.: US 9,243,207 B2
(45) Date of Patent: Jan. 26, 2016

(54) SOLVENT EXTRACTION OF PRODUCTS FROM ALGAE

(75) Inventors: Peter Domaille, San Diego, CA (US); Joe Toporowski, San Diego, CA (US); Judit Bartalis, San Diego, CA (US); Paul J. Berlowitz, Glen Gardner, NJ (US); Paul D. Oldenburg, Cypress, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 723 days.

(21) Appl. No.: 13/407,817

(22) Filed: Feb. 29, 2012

(65) Prior Publication Data

US 2013/0225846 A1    Aug. 29, 2013

(51) Int. Cl.
*C12N 1/00* (2006.01)
*C11B 1/10* (2006.01)
*C12M 1/00* (2006.01)

(52) U.S. Cl.
CPC ............... *C11B 1/108* (2013.01); *C12M 47/10* (2013.01)

(58) Field of Classification Search
None
See application file for complete search history.

(56) References Cited

U.S. PATENT DOCUMENTS

| | | | |
|---|---|---|---|
| 4,851,339 A | 7/1989 | Hills | |
| 5,979,473 A * | 11/1999 | Tate et al. | 134/66 |
| 7,868,195 B2 | 1/2011 | Fleischer et al. | |
| 8,115,022 B2 | 2/2012 | Kale | |
| 2007/0196383 A1* | 8/2007 | Murakami et al. | 424/195.17 |
| 2010/0099765 A1 | 4/2010 | Chilton et al. | |
| 2010/0181251 A1* | 7/2010 | Alspektor | 210/637 |
| 2010/0261922 A1* | 10/2010 | Fleischer et al. | 554/206 |
| 2011/0019085 A1 | 1/2011 | Chen | |
| 2011/0076748 A1 | 3/2011 | Salvo et al. | |
| 2011/0124544 A1 | 5/2011 | He et al. | |
| 2011/0195085 A1* | 8/2011 | Kale | 424/195.17 |
| 2011/0195168 A1* | 8/2011 | Wang | 426/490 |
| 2012/0288930 A1* | 11/2012 | Trimbur et al. | 435/317.1 |

FOREIGN PATENT DOCUMENTS

WO    2010104922 A1    9/2010

OTHER PUBLICATIONS http://web.archive.org/web/ 20101009062358/http://en.wikipedia.org/wiki/ Ethanol_(data_page); accessed May 7, 2015.*

* cited by examiner

*Primary Examiner* — Renee Claytor
*Assistant Examiner* — Michelle F Paguio Frising
(74) *Attorney, Agent, or Firm* — W. R. H. Clark; David M. Weisberg

(57) ABSTRACT

Processes for extracting product molecules from an algae feed are provided. The algae feed represents an input stream, batch sample, or other algae portion suitable for use in product extraction. The product extraction is typically performed at pressures greater than ambient pressure. This allows for improved extraction, including the potential for use of extraction solvents at temperatures greater than the boiling point for the solvent.

35 Claims, 5 Drawing Sheets

SOLVENT EXTRACTION OF PRODUCTS FROM ALGAE

FIELD OF THE INVENTION

Systems and methods are described for extracting molecules from algae, such as molecules suitable for use in fuel or fuel blending products.

BACKGROUND OF THE INVENTION

One potential source of biofuels is to generate molecules from algae that are suitable for making fuels. For example, algae, like plants, can generate lipid molecules. Some lipid molecules have a general structure and molecular weight suitable for making diesel fuel additives such as fatty acid methyl ester (FAME). It is also possible to refine certain algae lipids into conventional fuels or fuel blending stocks including gasoline, diesel, and jet fuel. However, many challenges remain in developing commercial scale production techniques for biofuels based on algae production.

One challenge in developing algae based biofuels is recovering desired product molecules from the algae. Algae cells include a variety of components. In addition to desired lipids and/or other product molecules made by the algae, a typical algae cell will also include proteins and other compounds that form the cell walls and the internal structures of the cell. In order to recover desired products, the desired products need to be separated from the cell walls and other compounds in the algae. Additionally, algae are typically grown in a pond at dilute concentrations. Recovery of desired products from algae requires separation of the desired products from a substantial amount of water.

U.S. Pat. No. 7,868,195 describes systems and methods for extracting lipids from dewatered wet algal biomass. A sample of wet algae biomass is centrifuged or filtered to reduce the water content. This results in a sample with a solids content of 10% to 40%. The dewatered sample is then mixed with an amphiphilic solvent such as dimethyl ether or an alcohol, ketone, or aldehyde containing 1 to 4 carbons. The mixture can be optionally heated. Solids are removed by filtration, centrifugation, or decanting, and the amphiphilic solvent can be separated from the water and lipids by evaporation of the solvent. The remaining water and lipid mixture is then phase separated to recover the lipids.

International Publication WO 2010/104922 describes a method for algae biomass fractionation. The method includes adjusting the pH of an aqueous sample of algae (or other sample of algae with a water-based polar solvent) to condition the algae cell walls for release of desired products. The conditioned algae sample is then contacted with a non-polar solvent. The mixture is partitioned to separate the polar and non-polar solvents. Products are then recovered from both the polar and non-polar solvent portions.

U.S. Patent Application Publication 2011/0195085 describes methods for performing solvent extraction of lipids and proteins from algae using methods that preserve the food grade integrity of the products. The methods include using alcohols and other solvents in sequential extractions at temperatures up to the boiling point of the solvent. The methods appear to be performed at ambient pressure.

SUMMARY OF THE INVENTION

In one aspect, the invention provides processes for extracting product molecules from an algae feed. The algae feed represents an input stream, batch sample, or other algae portion suitable for use in product extraction. The product extraction is typically performed at pressures greater than ambient pressure. This allows for improved extraction, including the potential for use of extraction solvents at temperatures greater than the normal boiling point for the solvent.

In another aspect, the invention provides methods for recovering products from algae. The methods include mixing an algae feed with particulate solids, the algae feed comprising from 0.1 wt % to about 30 wt % algae in water, the particulate solids having an average particle size between about 1 μm and about 200 μm, the dry weight of the particulate solids being at least about 10% of the weight of the algae feed; exposing the algae feed to a solvent under effective solvent extraction conditions, the effective solvent extraction conditions including a temperature of at least about 40° C. and a pressure of about 100 psig (0.7 MPag) to about 2500 psig (17.2 MPag), to form an extraction mixture comprising the solvent, the particulate solids, water, extracted products, and residual algae solids; and recovering at least a portion of the extracted products from the extraction mixture. Optionally, the methods can further include a washing step prior to exposing the algae feed to a solvent, wherein the algae feed is washed with water under effective washing conditions to produce a washed algae feed and a wash effluent. The washed algae feed is then exposed to the solvent.

In still another aspect, methods for recovering products from algae are provided. The methods include exposing an algae feed to a solvent under effective solvent extraction conditions, the algae feed comprising from 0.1 wt % to about 30 wt % algae in water, the effective solvent extraction conditions including a temperature of at least about 40° C. and a pressure greater than the vapor pressure of the solvent at the temperature, to form an extraction mixture comprising the solvent, water, extracted products, and residual algae solids; and recovering at least a portion of the extracted products from the extraction mixture.

In yet another aspect, methods are provided for recovering products from algae. The methods include washing an algae feed with water under effective washing conditions to produce a washed algae feed and a wash effluent, the algae feed comprising from 0.1 wt % to about 30 wt % algae in water; exposing the washed algae feed to a solvent comprising ethanol under effective solvent extraction conditions, the effective solvent extraction conditions including a temperature of at least about 50° C. and a pressure of about 14 psig (0.1 MPag) to about 200 psig (1.4 MPag), the pressure being greater than a vapor pressure of the ethanol at the temperature, to form an extraction mixture comprising the ethanol, water, extracted non-polar products, and residual algae solids; and recovering at least a portion of the non-polar extracted products from the ethanol.

In still another aspect, methods are provided for recovering products from algae. The methods include exposing an algae feed to an aqueous-based solvent under effective solvent extraction conditions, the algae feed comprising from 0.1 wt % to about 30 wt % algae in water, the effective solvent extraction conditions including a temperature of at least about 40° C. and a pressure greater than the vapor pressure of the solvent at the temperature, to form an extraction mixture comprising the aqueous-based solvent, extracted products, and residual algae solids; adding an organic solvent to the extraction mixture; separating the extraction mixture to form a first stream comprising at least 50 wt % of the water and at least 50 wt % of the residual algae solids and a second stream comprising at least 50 wt % of the organic solvent and at least 50 wt % of the extracted products; and recovering at least a portion of the extracted products from the solvent.

DETAILED DESCRIPTION OF THE EMBODIMENTS

Overview

Figure 1:
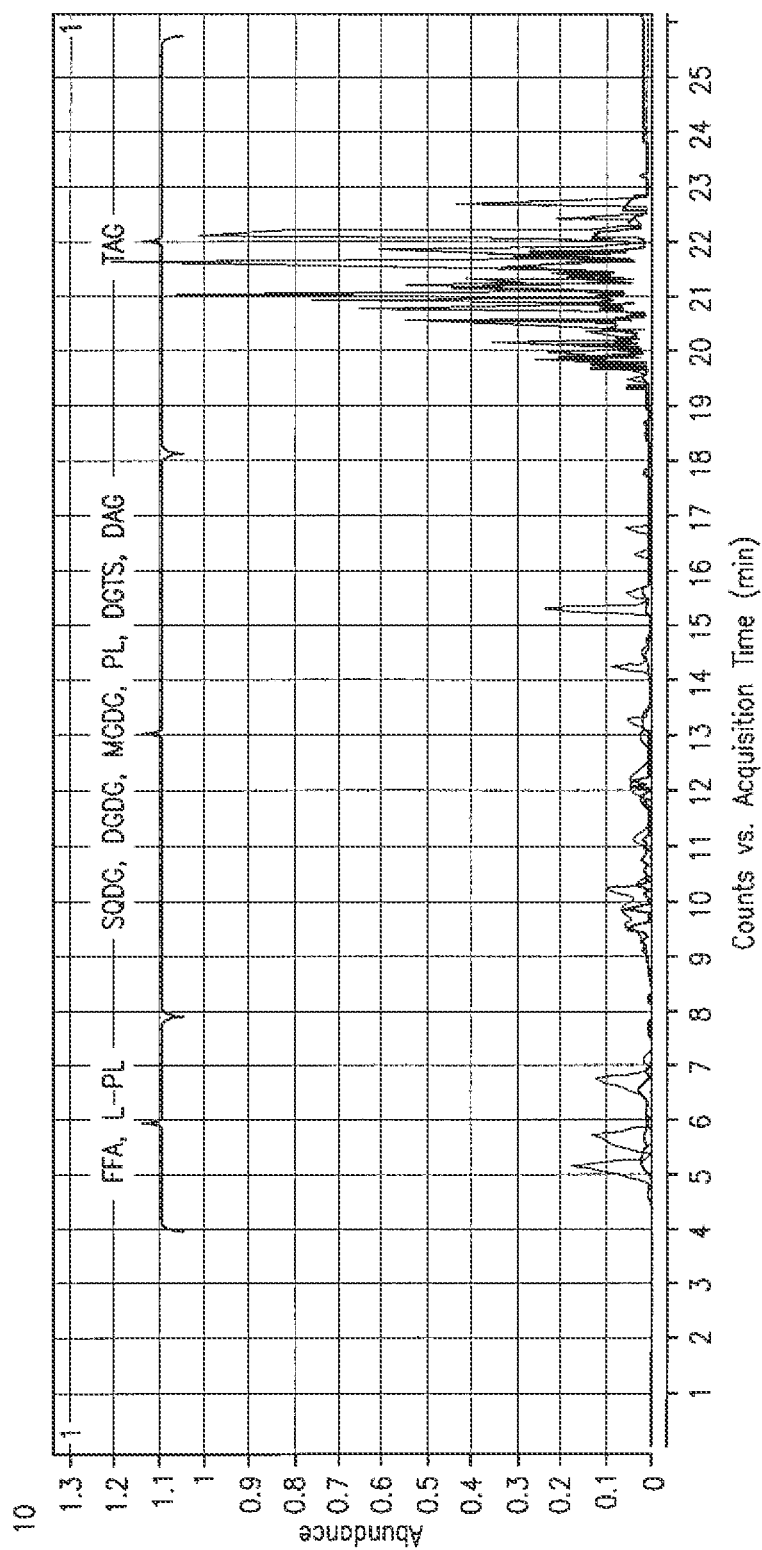
FIG. 1 shows a liquid chromatogram of lipids extracted from an algae sample and identified by mass spectrometry.

Systems and methods are described herein for extracting desired products, such as lipids or oils, from algae such as microalgae. The extracted products may be suitable for use (after optional further processing) as fuel or fuel blending products. The systems and methods allow for improved extraction efficiency of lipid or oil products in an abbreviated time frame. The systems and methods also reduce or mitigate the need to use specialized and/or expensive processing techniques to dewater the algae. The combination of improved extraction, reduced time, and reduced need to dewater the algae is enabled in part by using elevated pressures to assist the extraction process. The method of extraction includes several processes. First, some sample preparation may optionally be performed on the algae, in order to reduce the water content of the algae and/or mix the algae with another material to facilitate processing. An optional but preferred water wash of the algae sample can be performed before extraction. The optionally washed algae sample is then exposed to a solvent for extraction of the desired products, preferably at a pressure greater than ambient. After extraction, one or more separations are performed to concentrate and/or purify the desired extracted products.

Algae can be grown and harvested in order to extract desired organic products, such as oils or lipids suitable for use in a fuel product, fuel blending product, lubricant product, or lubricant blending product. Depending on the type of algae strain, the desired organic products will often boil in the distillate boiling range and/or are molecules, such as triacylglycerides, that are readily converted to distillate boiling range molecules. The distillate boiling range is defined herein to include molecules that boil from about 212° F. (100° C.) to about 1100° F. (593° C.), preferably about 250° F. (121° C.) to 750° F. (399° C.), and more preferably from about 300° F. (149° C.) to about 700° F. (371° C.). Narrower ranges within this definition may also be useful in order to meet product specifications such as a diesel product specification or a jet fuel product specification. Note that algae may also produce products outside of the distillate boiling range before, during, or after production of the desired distillate boiling range molecules. Such products outside of the distillate range may include naphtha (gasoline) boiling range molecules, or molecules with boiling points above the distillate boiling range. More generally, a desired product potentially includes any convenient organic species generated by algae. Suitable types of organic molecules include molecules with no functional groups (such as alkanes) as well as molecules with one or more types of functional groups, such as alcohols, amines, organic acids, other heteroatom functional groups, alkenes, aromatics, or other unsaturated functional groups. The desired products generated by algae may be used without further processing. Alternatively, further processing can be used to convert the desired algae products to other molecules, possibly including molecules having a different boiling range or molecules having a similar boiling range but with improved properties. Converted products may also be suitable for use or blending into gasoline for lighter components, or for use or blending into lubricants for molecules heavier than the preferred distillate boiling range.

Preparation of Algae for Extraction

Algae, such as microalgae, are typically grown in an aqueous environment, such as an open pond environment or a closed reactor environment that includes, in addition to the algal cells, an aqueous medium. The concentration of algae solids in the growth environment is typically low, such as less than about 0.3 wt % relative to the total weight of an aqueous algae sample. One of the challenges in extracting desired products from algae is to extract the desired products in a manner that eventually allows the products to be effectively and/or efficiently separated from the aqueous environment.

One option for improving the yield of extracted products is to substantially reduce the water content of an algae feed prior to extraction. "Algae feed" as used herein refers to algae harvested for the extraction, separation, or isolation of one or more algal products, such as, for example, proteins, pigments, nucleotides, peptides, carbohydrates, or lipids. Typically algae feed as disclosed herein includes microalgal cells that are at least partially or are substantially intact, although an algae feed can in some circumstances include algal cells that are at least partially lysed or ruptured. It is noted that the water present in an algae (or other biomass) feed can be either extracellular water or intracellular water. Intracellular water refers to water contained within the cell membrane of a cell, such as an algae cell. Algae feed that is apparently relatively dry based on extracellular water can still contain a substantial portion of intracellular water. In the discussion below, references to the amount of water in a feed relative to the amount of algae are on the basis of dry algae that does not contain intracellular water. Freeze-dried algae are an example of an algal feed that does not contain intracellular water. For an algal feed that contains intracellular water, computing the ratio of water to algae requires determining the amount of intracellular water, as any intracellular water should count toward the weight of water and not the weight of algae. As a clarifying example, an algae sample could include no extracellular water and still have a water to algae ratio of about 1 to 1 or greater, or about 2 to 1 or greater, due to the amount of intracellular water in the algae. More generally, references below to the weight of algae refer to the weight of dry algae, excluding intracellular water.

Conventional physical methods for water removal, such as centrifugation, filtration, flocculation, or dissolved air flotation can be used to increase the algae content of an algae feed. For some algae strains, physical methods can increase the algae content up to about 20 wt % to 30 wt % solids. For other algae strains that are more difficult to process, physical water separation may only increase the algae content up to about 10 wt % solids. Increasing the solids (algae) content beyond this point requires more expensive techniques, such as heating to evaporate the water. Removing water to achieve an algae content of between about 0.1 wt % to about 30 wt %, such as at least about 5 wt %, preferably at least about 7.5 wt %, is typically sufficient for performing methods according to the invention. This allows the use of more energy intensive and/or more costly water removal techniques to be minimized or avoided, if desired.

In addition to removing water, another potential preparation for the algae feed, which may be used alternatively or in addition to removing water as described above, is to mix the algae feed with a substance, such as particulate solids, that modifies the consistency of the algae. A dewatered algae sample can have a viscosity comparable to a fluid paste-like consistency. For batch or semi-batch type processing, it could be advantageous to increase the viscosity of the dewatered algae feed, to provide an algae feed that can be manipulated in a manner more like a solid. For example, after reducing water content to increase the relative algae content of the algae/water mixture, a particulate solid have a defined range of particle sizes can be added to the algae. Diatomaceous earth is an example of such a particulate solid. Diatomaceous earth is a substance containing mostly silica that is formed by certain types of algae (diatoms). The particle size of diatomaceous earth particles is typically from about 1 µm to about 200 µm. The amount of diatomaceous earth added to the algae feed can correspond to a weight ratio of algae feed to diatomaceous earth of from about 10:1 to about 1:2, such as at least about 1:1, and preferably at least about 2:1. Note that the algae feed includes the weight of both algae and water. Thus, the weight ratio of algae only relative to diatomaceous earth will be much lower, such as from about 2:1 to about 1:10.

More generally, other types of particulate solids can be added to the algae feed in place of or in addition to diatomaceous earth. Such particulate solids can have a range of particle sizes of from about 0.5 µm to about 250 µm, such as from about 1 µm to about 200 µm. Alternatively, particulate solids can be characterized based on an average particle size. Suitable average particle sizes can be about 200 µm or less, such as about 150 µm or less. A minimum average particle size can be selected to facilitate separation of the particulate solids from the desired products. For example, smaller particulate solids may be more difficult to remove by filtration or other physical separation methods. For non-spherical particles (i.e., particles with different lengths along different axes), the particle size and average particle size herein is defined based on the longest axis of the particle. As an example of another type of particulate solid, sand with an appropriate particle size may be suitable for use in place of diatomaceous earth. Sand with a 400 mesh size has an average particle diameter of about 37 µm. This is comparable in particle size to diatomaceous earth. Still another option for a particulate solid can be a silica gel having particles with a suitable average particle size as described above.

Although adding diatomaceous earth does not increase the algae content of an algae/water mixture, the diatomaceous earth will increase the overall solids content of the mixture. This can increase the viscosity of the mixture. For example, an initial dewatered algae sample may have a viscosity similar to a slurry. Adding diatomaceous earth (or another suitable particulate solid) can increase the viscosity of the algae sample so that the algae sample has a consistency similar to wet sand. The amount of change in viscosity can be modified by changing the relative amount of diatomaceous earth added to an algae feed. Additionally, the diatomaceous earth can provide a matrix or support for the algae. Without being bound by any particular theory, when diatomaceous earth is mixed with an algae sample, it is believed that the algae solids become adsorbed or otherwise trapped by the surrounding matrix of diatomaceous earth particles. Because diatomaceous earth is primarily composed of silica, diatomaceous earth particles will typically retain their shape and size when exposed to pressure, such as when a fluid containing diatomaceous earth particles is passed through a filter. This is in contrast to many types of algae solids, which may tend to pack and/or compress against a filter surface during filtration. Such packing or compression of algae solids at a filter surface can lead to an increase in the pressure drop required to pass fluids through a filter. As a result, if a filtering step is used to separate liquids from the algae/diatomaceous earth mixture, the diatomaceous earth will reduce or minimize the tendency of the algae to compact against the filter. Instead, an algae sample mixed with diatomaceous earth will tend to retain a size based on the amount of diatomaceous earth present, with the algae solids being retained within the diatomaceous earth particles. Products can subsequently be more efficiently extracted from the non-compacted algal sample, preferably without requiring vigorous agitation of mixing to ensure sufficient contact of the solvent with the algal solids.

Diatomaceous earth also may provide additional advantages relative to some other types of particulate solids, such as sand. For example, if an algae feed is washed with water under relatively severe conditions that are able to remove non-product compounds (such as protein and carbohydrates), such as a pressure of at least about 300 psig (2.1 MPag), and/or a temperature of greater than 20° C., some desired lipid or oil products from the algae could potentially be released from the cells during the water wash. However, if the algae feed is mixed with diatomaceous earth, the diatomaceous earth is believed to assist in retaining the desired lipid products in the algae/diatomaceous earth mixture during such a wash. The retained lipids are then available for removal in a subsequent solvent extraction step. Other types of particulate solids, such as sand, may have less ability to retain desired lipids during a water wash, resulting in extraction of a portion of lipids prior to the desired time in the extraction step.

Diatomaceous earth is a silica-rich rock or powder derived from the frustules of some types of algae, namely the Bacillariophyceae, or diatoms. If a diatom species is used as the algae for product extraction, additional diatomaceous earth (or a similar silica-rich composition) may be recovered from the residual algae solids after product extraction for use in future extractions.

Optional Water Wash

As an optional initial step to all of the methods of the invention described herein, an algae feed can be washed with water prior to extraction of desired products. As further described below, the water wash can be performed at ambient temperature and pressure, or at least one of the temperature or pressure can be elevated relative to ambient conditions. This optional initial process can remove at least a portion of ionic impurities (e.g. salts) or other non-lipid compounds present in the algae feed. Without being bound by any particular theory, this initial process may also assist in disrupting algae cell membranes to make the desired product molecules more accessible to the solvent.

Algae are typically grown in an aqueous environment that contains a variety of water soluble metal salts, including NaCl. When algae are harvested to form an algae feed, a portion of the algal culture medium is typically harvested with the algae. Performing an initial water wash of an algae feed allows at least a portion of such metal salts to be removed from the algae feed prior to introducing an extraction solvent. This reduces the amount of impurities that need to be removed from the desired products after extraction.

A water wash can also assist with disrupting cell membranes or otherwise facilitating removal of desired products from algae cells while removing non-lipid organic compounds from the sample that will subsequently be extracted. If the water wash is conducted at ambient pressure, the wash will typically remove only material that is already outside of the algae cells, such as salts that were present in the algae growth environment prior to harvesting of the algae to form the feed. A water wash at a higher pressure, however, can remove additional materials. For example, exposing an algae feed to a water wash at a pressure of about 1500 psig (10.3 MPag) to about 1700 psig (11.7 MPag), a temperature of about 20° C. to about 50° C., and an exposure time of about 2 minutes to 15 minutes will also remove a portion of proteins and/or carbohydrates from the algae sample. The proteins and carbohydrates may be water soluble allowing the molecules to be carried away in the water wash.

More generally, a variety of effective water wash conditions can be used. A water wash can be performed in a batch, semi-batch, or continuous mode. Suitable effective pressures for the water wash include from a roughly ambient pressure (i.e., not pressurized relative to external environment, or no gauge pressure) or alternatively about 14 psig (0.1 MPag) up to about 2500 psig (17.2 MPag). Examples of potential ranges for operation include a low pressure range from about ambient or alternatively about 14 psig (0.1 MPag) to about 100 psig (0.7 MPag). Another option is to operate at a medium pressure from about ambient or alternatively about 14 psig (0.1 MPag) up to about 500 psig (3.4 MPag), such as from about 100 psig (0.7 MPag) to about 300 psig (2.1 MPag). Still another option is to operate at a high pressure from about ambient or alternatively about 100 psig (0.7 MPag) up to about 2500 psig (17.2 MPag), such as from about 300 psig (2.1 MPag) to about 2000 psig (13.8 MPag), preferably from about 300 psig (2.1 MPag) to about 1700 psig (11.7 MPag), more preferably 500 psig (3.4 MPag) to about 1000 psig (6.9 MPag). If a gas is added to a reaction system to achieve the desired pressure during the water wash, an inert gas such as $N_2$ may optionally be used. Suitable effective temperatures for the water wash range from about 20° C. (or alternatively about ambient) to as high as 200° C. such as from 25° C. to 150° C., or preferably from about 25° C. to 100° C., and can be, for example between about 25° C. and 80° C., or between about 40° C. and 80° C. In some examples, the temperature range for the water wash range may be from about 40° C. to 60° C., or from about 40° C. to 50° C.

The type of water used for the water wash can depend on the water wash conditions and the eventual use of the effluent from the water wash. If the water wash conditions are effective for removal of a portion of proteins and/or carbohydrates, it may be desirable to recover the proteins and/or carbohydrates from the water wash effluent. In this type of situation, it is preferable to use a fresh or clean water source for the water wash to reduce or minimize the introduction of additional impurities. Alternatively, if the water wash effluent will be used as an input stream to provide water for an algae growth environment, a portion of the water wash effluent can optionally be recycled for use in washing the next batch or portion of algae. Still another option is to use water from an algae growth environment, such as a filtered stream of pond water from an algae growth pond.

The amount of time for exposing algae to the water wash can vary depending on the reaction conditions. Suitable effective times range from about 1 minute to about 20 minutes, such as about 2 minutes to about 10 minutes. The amount of water used in the water wash can also vary. In a batch type configuration, the weight of water used for the water wash may be comparable to the weight of the algae feed, such as a ratio of wash water to algae feed of about 1:2 to about 3:1. The wash water can be removed from the algae feed by any convenient means, such as using a pressure differential to remove water from the processing vessel or centrifugation. Note that the algae feed contains about 30 wt % or less algae in water. Thus, at low ratios of wash water to algae feed, the amount of wash water may be less than the amount of water already present in the algae feed.

In a configuration where at least the wash water has a continuous flow, it may be desirable to use larger ratios of wash water to algae feed. If a relatively low amount of desired products are expected to be removed in the water wash, so that product recovery does not need to be performed on the wash effluent, a larger flow of water will pose fewer problems. Suitable weight ratios of wash water to algae feed can range from about 1:2 to about 5:1 or greater.

The composition of the effluent from the water wash process will vary depending on the water wash conditions. Under mild conditions, such as a pressure of 100 psig (0.7 MPag) or less, the effluent will primarily contain water soluble metal salts such as NaCl. Under higher pressure conditions, such as 300 psig (2.1 MPag) or greater, the water wash may also include proteins and/or carbohydrates from the algae cells. The amount of material dissolved or partially dissolved in the water wash can be characterized by evaporating the water to leave behind the solvated material. Depending on the embodiment, dissolved salts can make up from about 70 wt % to 100 wt % of the solvated material, with the remainder of the solvated material corresponding to proteins and carbohydrates. Note that this represents only the dissolved or partially dissolved material. Other non-soluble algae solids may also be entrained in the water wash.

If a water wash is performed, at least a portion of the effluent can optionally be recycled for further use. The recycling use and any processing before or during recycling can depend on the composition of the wash effluent. For a wash effluent that primarily contains water and ionic salts, the wash water can be recycled to the growth environment. A wash effluent containing proteins and/or carbohydrates can also be recycled. Optionally, a wash effluent can also be further processed to recover and/or modify the organic material prior to recycling. As an example of further processing, any proteins, carbohydrates, or other organic material in the wash effluent can be separated out from the effluent and then exposed to an anaerobic digestion process. Such a process would allow for recovery of nitrogen and phosphorous while also generating $CO_2$. The separated nutrients, optionally including $CO_2$, could then be recycled in a controlled manner so that desired algae growth conditions are maintained. Further processing of a wash effluent prior to recycling can reduce or mitigate any potential modifications of the conditions within the growth environment due to recycling, such as supplying an organic compound that may cause heterotrophic or mixotrophic metabolic changes in an algal culture intended to be photoautotrophic, or supplying an organic compound that may support the growth of deleterious organisms.

Alternatively, a first water wash can be performed at non-elevated temperature and non-elevated pressure to produce an effluent that includes primarily non-organic nutrients such as salts. Non-elevated temperatures for a water wash refer to temperatures of less than about 40° C., such as less than about 35° C. or 30° C. Non-elevated pressures for a water wash refer to pressures that differ from an ambient pressure by less than about 10 psi (69 kPa), such as differing from ambient pressure by less than 1 psig (6.9 kPag). This first water wash effluent can be recycled to the algal growth environment. A second water wash at elevated temperature and/or elevated pressure can then be performed in which at least a portion of the algae are lysed during the wash, where organic compounds can be released from the cells, including the external surface of the cells, the interior of the cells, or a combination thereof. Elevated temperatures and/pressures for a water wash are temperatures and/or pressures above non-elevated conditions, such as any of the previously described temperature and pressure conditions for a water wash. The effluent of the second water wash can optionally be directed to a fermenter or anaerobic digester.

The effluent of a water wash can optionally be treated prior to directing the nutrients in the water wash to a fermenter or digester. For example, the effluent can be treated with acid or base or other compound to precipitate one or more proteins, carbohydrates, or other algal products, or can be filtered or run over a column, where one or more separated algal products or the wash fraction from which an algal product has been removed can be added to the algal growth environment, added to a digester or fermenter, or further purified or treated for other uses. These optional treatments can be used on any convenient water wash effluent, including water wash effluents generated under elevated or non-elevated temperature and pressure conditions.

Solvent Extraction of Products at Elevated Pressure

After the optional water wash, the algae can be exposed to a solvent at elevated pressures for extraction of desired products. Conventionally, solvent extraction is performed without attempting to separately increase the pressure in the reaction process. In such a conventional extraction, the temperature of the extraction is limited by the boiling point of the solvent. If the volume of the reaction chamber is not too large relative to the amount of solvent, some pressure increase may occur as the solvent is vaporized. However, this still limits a solvent extraction process to combinations of pressure and temperature that are correlated with the vapor pressure curve of the solvent.

Solvent extraction according to the invention may be performed in a reaction system under effective conditions for extraction of one or more desired products. In some preferred embodiments, the effective conditions include using a pressure greater than ambient pressure during at least a portion of the method. Performing the extraction at an elevated pressure provides a variety of potential advantages. An elevated pressure increases the boiling point for a solvent to a temperature above the regular boiling point (i.e. the boiling point at 1 atmosphere of pressure). This allows higher temperatures to be used without approaching the solvent boiling point and therefore system energy goes into heating rather than promoting phase changes. An elevated pressure also appears to reduce the required time for effective extraction of desired products. For example, effective processing conditions can include a pressure in the reaction vessel that is at least about 50% greater than the corresponding vapor pressure of the solvent at the processing temperature, such as at least about 100% greater, or even at least about 200% greater. Still higher pressures during solvent extraction may also be useful for achieving other benefits of processing at elevated pressure.

The solvent used for extraction may depend in part on the desired method for separating the desired product lipids and/or oils from the solvent after extraction. One option is to use an organic solvent that is at least partially miscible with water. Suitable organic solvents that are miscible with water include methanol, ethanol, other alcohols containing 4 carbons or less, ketones containing 4 carbons or less, cyclic ethers such as dioxane and tetrahydrofuran, and acetonitrile. Another option is to use an organic solvent that is immiscible or that has low miscibility with water, such as alkanes, methyl tert-butyl-ether, chloroform, dichloromethane, or ethyl acetate. Yet another option is to use water for the extraction. Each of these options is discussed in greater detail below.

Suitable effective pressures for solvent extraction can range from a roughly ambient pressure (i.e., not pressurized relative to external environment, or zero gauge pressure) or alternatively a pressure of about 14 psig (0.1 MPag) up to about 2500 psig (13.8 MPag). Examples of potential ranges for operation include a low pressure range from about ambient or alternatively about 14 psig (0.1 MPag) to about 100 psig (0.7 MPag). Alternatively, a low pressure range can be from about 14 psig (0.1 MPag) to about 200 psig (1.4 MPag). Another option is to operate at a medium pressure from about ambient or alternatively about 14 psig (0.1 MPag) up to about 500 psig (3.4 MPag), such as from about 100 psig (0.7 MPag) to about 300 psig (2.1 MPag). Still another option is to operate at a high pressure from about ambient or alternatively about 100 psig (0.7 MPag) up to about 2500 psig (17.2 MPag), such as from about 300 psig (2.1 MPag) to about 2000 psig (13.8 MPag), preferably from about 300 psig (2.1 MPag) to about 1700 psig (11.7 MPag), more preferably 500 psig (3.4 MPag) to about 1000 psig (6.9 MPag). If a gas is added to a reaction system to achieve the desired pressure during the water wash, an inert gas such as $N_2$ can be used.

Suitable effective temperatures for solvent extraction range from about 40° C. (or alternatively about ambient) to 200° C., such as from 50° C. to 150° C. One option is to use an elevated pressure to allow for extraction at higher temperatures without reaching the boiling point for the solvent. Depending on the solvent, a temperature above the normal boiling point of the solvent can be a temperature from about 80° C. to about 200° C. The amount of time for exposing algae to the water wash can vary depending on the reaction conditions. Suitable effective times range from about 10 minutes to about 120 minutes, such as about 10 minutes to about 60 minutes, preferably about 15 minutes to 30 minutes.

One option for the solvent extraction is to use a water miscible solvent such as an alcohol, ketone, or cyclic ether. Examples of suitable solvents include methanol, ethanol, propanol, isopropanol, isobutanol, n-butanol, acetone, and tetrahydrofuran. Other examples include alcohols or ketones having a ratio of carbon to oxygen of about 4:1 or less, cyclic ethers such as dioxane and tetrahydrofuran, water miscible ethers such as diethyl ether, other oxygen-containing organic molecules having a ratio of carbon to oxygen atoms of about 4:1 or less, and other polar organic molecules that are liquids at ambient temperature and pressure such as acetonitrile. Exposing algae to a water-miscible solvent under effective extraction conditions will result in desired products (such as oils and/or lipids) being extracted into the solvent phase. The solvent and product phase will also typically include some residual water. This water can be from the prior optional water wash or can correspond to the initial water in the algae sample.

The amount of solvent used for the solvent extraction can depend on a variety of factors. A typical ratio of the weight of solvent relative to the weight of dry algae can be a solvent to algae ratio of from about 1.0:1.0 up to about 10.0:1.0 or 15.0:1.0. For example, the weight ratio of solvent to dry algae can be from about 1.5:1.0 to about 5.0:1.0. It is noted that the ratio of water to algae solids in the algae sample before the water wash is between about 5.0:1.0 and 10.0:1.0. A portion of this water will mix with the solvent during extraction. As a result, the ratio of solvent to water in the extraction effluent may be from about 5.0:1.0 to as low as about 1.0:1.0.

Another way of characterizing the amount of solvent is based on the amount of oil to be extracted. Preferably, the weight ratio of solvent to algae oils is about 15:1 or less. Part of the goal for limiting the amount of solvent relative to the amount of recovered oil is to limit the amount of energy that is expended in recovering algae oil from the solvent as compared to the energy content of the recovered oil. For example, the weight ratio of solvent to algae oil can be selected so that the amount of energy required for separating the solvent from the oil is 15% or less of the energy content of the oil. For an alkane solvent such as heptane, this corresponds to about a 15:1 weight ratio or less of solvent to oil. For ethanol, this corresponds to about a 13:1 weight ratio of ethanol to solvent, but this excludes any additional energy needed for azeotropic distillation.

When a water-miscible solvent is used for extraction, the resulting extraction effluent (a solvent/water mixture containing lipids and/or oils) may have a cloudy appearance. One method for recovering the lipids and/or oils from the solvent/water mixture is to distill off the solvent and water, leaving behind the desired products. While such distillation is effective, recovery processes that involve boiling of water require higher ratios of energy spent (in the form of fuel for heating) to energy recovered (in the form of fuel molecules). As a result, other options that are less energy intensive may be preferable. Another option is to decrease the solubility of the desired lipid or oil products by modifying the solvent/water mixture, and then separate the desired products by gravity. For example, the extracted lipids and/or oils are typically soluble in the solvent but not in water. As the amount of water in the solvent/water mixture increases, the solubility of the lipids and/or oils will decrease, leading to increasing amounts of phase separation in the solvent/water mixture. Initially this phase separation corresponds to a cloudy appearance in the solvent/water mixture. As additional water is added to the mixture, the lipids and/or oils will segregate into a separate (possibly solid) phase. Inducing this phase separation by increasing the water content of the solvent/water mixture represents one method for separating the desired lipid and/or oil product(s) from the solvent. However, this method also results in mixing the extraction solvent with large quantities of water. Recovery of the extraction solvent requires separation of the extraction solvent from water, such as by distillation.

Some improvement in separation of the extraction solvent from water can be achieved by using a solvent with a lower miscibility in water, such as butanol or isobutanol. Butanol and isobutanol have limited solubility in water. Additionally, butanol does not form a homogenous azeotrope, so methods for performing a complete separation of butanol and water are less energy intensive than methods for separating ethanol and water.

When using a water miscible solvent, such as ethanol, the severity of the reaction conditions can impact the type of products recovered during extraction. For example, at lower severity conditions, such as a temperature of about 50° C. to about 80° C. and a pressure of about 14 psig (0.1 MPag) to about 200 psig (1.4 MPag), the extraction process can effectively extract non-polar lipids from the algae feed, but polar lipids may have a lower extraction efficiency. In this type of embodiment, the pressure should be selected to be greater than the vapor pressure of the solvent at the extraction temperature. Under more severe temperature and/or pressure conditions, the extraction will have increasing effectiveness in also extracting the polar lipids.

Another option is to use an extraction solvent with a lower miscibility in water, or possibly a solvent that is immiscible with water. Alkanes such as n-heptane, dichloromethane, or alcohols with more than 4 carbons provide examples of lower miscibility and/or immiscible extraction solvents. Other examples of suitable solvents include non-polar organic liquids, such as aliphatic hydrocarbons, or various petroleum ethers. Still other suitable solvents include esters, ethers, ketones, nitrated and chlorinated hydrocarbons. Yet other examples of solvents include carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, or 2,2,4-trimethylpentane. Still other options include petroleum streams such as kerosene, naphtha or distillate streams, either as virgin crude cuts or as finished refinery products. Synergies may be found when selected petroleum streams that will be subjected to similar downstream processing as the extracted algae oils and/or lipid products (such as hydrotreating and/or isomerization) are used as an immiscible solvent. In such cases, solvent does not need to be recovered by distillation for recycle, but will accompany the recovered algae oils and/or lipid products into finished products.

Due to the limited solubility of alkanes or other lower miscibility solvents, the effluent from solvent extraction will typically include at least an aqueous phase and a solvent phase containing the extracted oil or lipid products. In this type of embodiment, any convenient method for separating distinct liquid phases can be used to separate the aqueous and solvent phases. Examples include using a gravity settling separator or a centrifuge. The desired product(s) can then be recovered from the solvent phases, such as by evaporation or distillation. Because the solvent phase will have little or no water content, evaporation of the solvent to recover lipids and/or oils is more favorable than evaporating a water-based solvent. In an integrated process, it is typically desirable to recover the solvent by fractionation, so that the recovered solvent can be recycled for subsequent oil and/or lipid product extractions. If desired, any excess solvent that is retained in the aqueous phase after separation can be removed for recycling by distillation.

Still another option is to use water as the extraction solvent. Although oils and lipids have limited solubility in water, the oils and/or lipids can still become entrained in water as an extraction solvent under effective extraction conditions. For example, the dielectric constant of water tends to decrease with increasing temperature. At 300° C., the dielectric constant of water is about 22, which is similar to the dielectric constant of acetone. As a result, increasing the temperature of water can be effective for increasing the corresponding solubility of organic molecules (such as oils and/or lipids) in water. The oils and/or lipids can then be separated from the water by any suitable method, such as physical separation (centrifugation, gravity settling) or adding an immiscible or partially miscible solvent to extract the oils and/or lipids from the water phase. These physical separation techniques can be further enhanced by performing the physical separation at a lower temperature than the extraction temperature, for at least the reasons noted above.

Any of the above extraction methods can be used as part of a batch, semi-batch, or continuous process for solvent extraction. The extraction methods are described herein as a single extraction step for convenience in explaining the nature of the various embodiments. However, any of the extractions according to the invention can be performed as a series of multiple extractions if desired. Combinations of different extraction types can also be used consecutively if desired. In many embodiments, the majority of the desired oil and/or lipid product(s) will be extracted in the first extraction performed on algae. As a result, subsequent extractions may yield a reduced or minimal amount of additional oil and/or lipid products. The extracted oil and/or lipid product can be used in various examples for the production of a fuel, fuel additive, surfactant, or lubricant.

Any of the separations described can be batch, semi-batch, or continuous. In separations involving more than 2 components, the separation step can include more than one type of separator that can be optimized for separation of different target components.

Process Recycle and Integration

To enhance the renewable character of the products extracted from the algae feed, various types of process integration are desirable. The integration can include recycling of output flows from various parts of the algae extraction process as well as use of output flows as inputs for additional biomass growth.

In addition to the desired extracted products, an algae extraction process generates a variety of other output streams. Each of the additional output streams provides a potential opportunity for recycling and/or integration with other processes. Depending on the embodiment, the additional output stream may include a water wash effluent, a diatomaceous earth stream, one or more solvent streams, one or more additional water streams, and/or a residual algae solids stream. In some embodiments, one or more of the output streams may exit the algae extraction process as a combined stream that requires separation before further recycling or integration.

One source of material for further processing is the algae extraction residue that is produced during extraction. The algae extraction residue will include residual algae solids, such as algal husks and other cell material that is not extracted as a product. Some of the algae residue may also be in the form of a liquid. The method for recycling or re-using the algae extraction residue can depend on the nature of the extraction process. In embodiments where particulate solids are mixed with the algae feed, at least a portion of the residual algae solids will remain mixed with the particulate solids after extraction. Recycle of both the particulate solids and the residual algae is dependent on separating this mixture. One option is to burn the residual algae solids to generate heat and $CO_2$. The $CO_2$, after optional purification, can be used as a nutrient for algae growth. Heat exchangers can be used to transfer the heat from burning the residual algae solids to another process, such as the water wash or the extraction process. After burning off the algae extraction residue (typically in the form of residual algae solids), the particulate solids can be recycled for use in processing additional algae.

Another recycling option is to perform a digestion process, such as anaerobic digestion, on the algae extraction residue. In addition to carbon, a portion of residual biomass (such as an algae extraction residue) will typically include phosphorous compounds, nitrogen compounds, and other trace metals in some form. This residual biomass can be converted into a form suitable for use as nutrients by an anaerobic digestion process. Anaerobic digestion refers herein to the enzymatic breakdown of organic material into simpler molecules or compounds by bacteria in an environment that lacks oxygen ($O_2$). In an anaerobic digestion process, the algal by-products are exposed to bacteria, including but not limited to methanotropic bacteria, that convert the remaining by-products into a more usable form. Typical digestion products include hydrogen, small volatile organic molecules such as methane. $CO_2$, and a variety of compounds containing phosphorous, nitrogen, and/or trace metals. The hydrogen and small organic molecules are typically suitable for use as a fuel while the $CO_2$ and other residual compounds can be recycled to an algae growth pond (or other algae growth environment) as nutrients. In addition to recycling the digestion products, the particulate solids remaining after anaerobic digestion can also be recycled.

Digestion and/or burning of the algae extraction residue can also be performed in embodiments that do not involve particulate solids. Depending on the type of algae and the extraction conditions, fermentation of the algae extraction residue to form alcohols or other small organics may also be feasible. After solvent extraction of lipid products, some forms of algae will produce an algae extraction residue that includes saccharides, polysaccharides, starches, and/or other potentially fermentable material. Prior to fermentation, it may be desirable to perform a hydrolysis process and/or enzyme treatment, or another type of pre-fermentation processing on the algae extraction residue. Any fermentable material in the algae extraction residue can then be fermented using a suitable yeast (e.g., *Saccharomyces cerevisiae*) or a suitable bacterium to form oxygenates. The type of oxygenate formed is typically dependent on the type of yeast or bacteria. Possible oxygenates include alcohols, such as methanol, butanol, or ethanol, or organic acids such as acetic acid. Examples of yeast or bacteria include Enterobaceriae, which can produce organic acids, and the yeast *Saccharomyces cerevisiae* which is useful for ethanol production.

During fermentation, the yeast or bacteria consume the fermentable material and form oxygenates, $CO_2$, and heat. Fermentation also typically results in formation of some residual by-products. A separator can be used to separate out the gas phase $CO_2$, the aqueous phase oxygenates, and the now insoluble by-products. The $CO_2$ can be recycled for any convenient use. For example, the $CO_2$ can be returned to an algae growth pond for use in growth of a new batch of algae.

The aqueous phase containing oxygenates is then distilled to concentrate the desired oxygenates in the aqueous environment. The water removed during distillation can be recycled, for example, to an algae growth pond. The oxygenates can be used in a variety of ways. For example, the fermentation conditions may be selected to form alcohols, acids, or a combination thereof that correspond to the solvent used for solvent extraction. Such solvent molecules generated from algae extraction residue can be used to replace solvent lost during the extraction process due to incomplete separation.

The water and solvents used during processing can also be recycled for further use. After extraction of desired products, various types of separation processes can be used to separate the extraction solvent from water. For a non-miscible solvent, a majority of the separation can be performed using physical processes, such as settling tanks, centrifuges, and other methods for separating distinct liquid phases. For miscible or partially miscible solvents, distillation can be used to separate solvents from water. For solvents such as ethanol, azeotropic distillation may be used to perform a more complete separation. After recovery, the solvent may be recycled for use in processing additional algae. The water can also be used for any convenient purpose, such as use in a water wash or as a water source for an algae growth environment.

Types of Algae

Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui, Nannochloropsis gaditiana. Dunaliella salina. Dunaliella tertiolecta, Chlorella vulgaris, Chlorella variabilis*, and *Chlamydomonas reinhardtii*. Additional or alternate algal sources can include one or more microalgae of the *Achnanthes, Amphiprora, Amphora, Ankistrodesmus, Asteromonas,*

*Boekelovia, Borodinella, Botryococcus, Bracteococcus, Chaetoceros, Carteria, Chlamydomonas, Chlorococcum, Chlorogonium, Chlorella, Chroomonas, Chrsosphaera, Cricosphaera, Crypthecodinium, Cryptomonas, Cyclotella, Dunaliella, Ellipsoidon, Emiliania. Eremosphaera, Ernodesmius, Euglena, Franceia, Fragilaria, Gloeolhamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus. Platymonas, Pleurochrsis, Pleurococcus, Prototheca, Pseudochlorella, Pyramimonas, Pvrobotrys, Scenedesmus, Skeletonema, Spyrogyra, Stichococcus, Tetraselmis, Thalassiosira, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylcoccopsis, Dermocarpella, Fischerella, Fremyella, Geitleria, Geitlerinema, Gloeobacter, Gloeocapsa, Gloeothece, Halospirulina, Ivengariella, Leptolyngbya, Limnothrix, Lyngbya, Microcoleus, Microcystis, Mxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scvtonema, Spirulina, Stanieria, Starria, Stigonema, Symploca, Synechococcus, Svnechocystis, Tolipothrix, Trichodesmium. Tychonema*, and *Xenococcus* species.

Algae oils or lipids are typically contained in algae in the form of membrane components, storage products, and metabolites. Certain algal strains, particularly microalgae such as diatoms and green algae, contain proportionally high levels of lipids. Algal sources for the algae oils can contain varying amounts, e.g., from 2 wt % to 40 wt % of lipids, based on total weight of the biomass itself.

Example

Pressurized Hot Ethanol Extraction

To demonstrate the effectiveness of solvent extraction of algae products at elevated pressures, a laboratory scale extraction was performed using ethanol as a solvent. A proprietary strain of *Cyclotella* algae culture was harvested and then dewatered using a centrifuge. This resulted in an algae sample with a paste-like consistency. The sample included about 90% water and about 10% algae solids. The 90% water includes culture medium from the algae growth environment which contains dissolved salts. The algae sample was then mixed in a 5:3 by weight ratio with diatomaceous earth. This modified the consistency of the algae sample so that the sample could be readily scooped. A 66 ml zirconium cell was then loaded in the following manner. The bottom of the cell included a 10 μm frit. A 1.3 μm GF/B glass fiber filter was placed on top of the frit. A thin layer of diatomaceous earth was placed on top of the glass fiber filter. A 48 gram sample (30 grams algae paste, 18 grams diatomaceous earth) was then loaded into the cell on top of the diatomaceous earth pad layer. A layer of 20-30 mesh sand was added to the top of the cell to fill any remaining volume.

Fresh water (such as deionized water or other non-salt water) was then added to the cell and pressurized with nitrogen gas. The cell was heated to 40° C. for 4 minutes, and the water was then expelled from the cell under pressure through an opening in the bottom of the cell. After exiting the chamber, the water was collected and evaporated. This resulted in a residue that was about 75% salt (primarily NaCl) and about 25% organic material (primarily proteins and carbohydrates).

After the water wash, 100% ethanol was added to almost fill the cell. The cell was then sealed and pressurized to about 1500 psig to 1700 psig with nitrogen gas. The cell was heated to about 120° C. and maintained under the temperature and pressure conditions for 15 minutes. The ethanol was then expelled through the filter via pressure differential to exit through the opening in the bottom of the chamber. This resulted in a cloudy extraction effluent. Due to the prior water wash, the ethanol contained some water. The oils and/or lipids extracted from the algae were believed to not be completely soluble in the wet ethanol, resulting in the cloudy appearance of the extract. Rotary evaporation was used to dry the wet ethanol, leaving behind an extract residue. The extract residue was re-dissolved in 100% ethanol at 55° C. and then filtered through a GF/B glass filter to remove insolubles. Rotary evaporation was used again to remove the ethanol, leaving behind a desired lipid and/or oil product. Recovery efficiency was measured as 99-103% in repeats of several runs.

The above washes and extractions can be performed in any convenient type of apparatus. An example of a suitable apparatus for a laboratory scale test is an ASE® 350 Accelerated Solvent Extractor available from Dionex Corporation.

FIG. 1 shows a chromatographic profile of intact polar and neutral lipids from the desired product. The chromatograph was generated by Reverse-Phase High Performance Liquid Chromatography coupled to Electrospray Ionization High Resolution Quadrupole Time of Flight Mass Spectrometer (LC/MS). The chromatograph shows various types of product species, including free fatty acids (FFA); lyso polar lipids (PL) of phosphatidylethanolamine (PE), phosphatidylglycerol (PG), and phosphatidylcholine (PC); sulfoquinovosyl diacylglycerol (SQDG): digalactosyl- and monogalactosyl diacylglycerol (DGDG. MGDG); diacylglycero-trimethylhomoserine (DGTS), diacylglycerol (DAG); and triacylglycerol (TAG). The FFA, PE, PG, and SQDG species were monitored by negative ionization, while the rest were monitored by positive ionization. As shown in FIG. 1, TAG lipids represent a majority of the product recovered.

Figure 2:
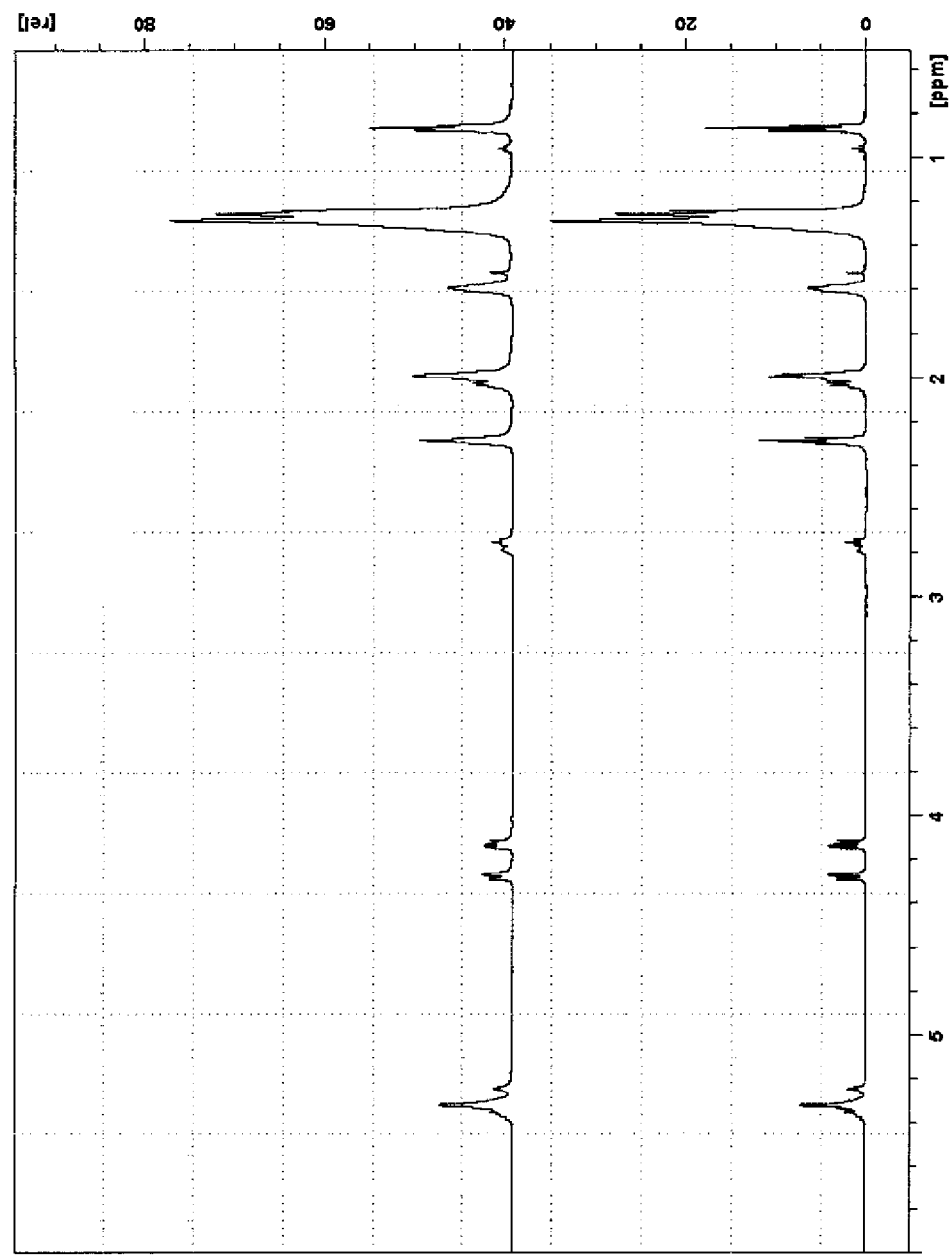
FIG. 2 shows $^1$H NMR spectra of a sample of extracted lipids and a reference sample.
Figure 3:
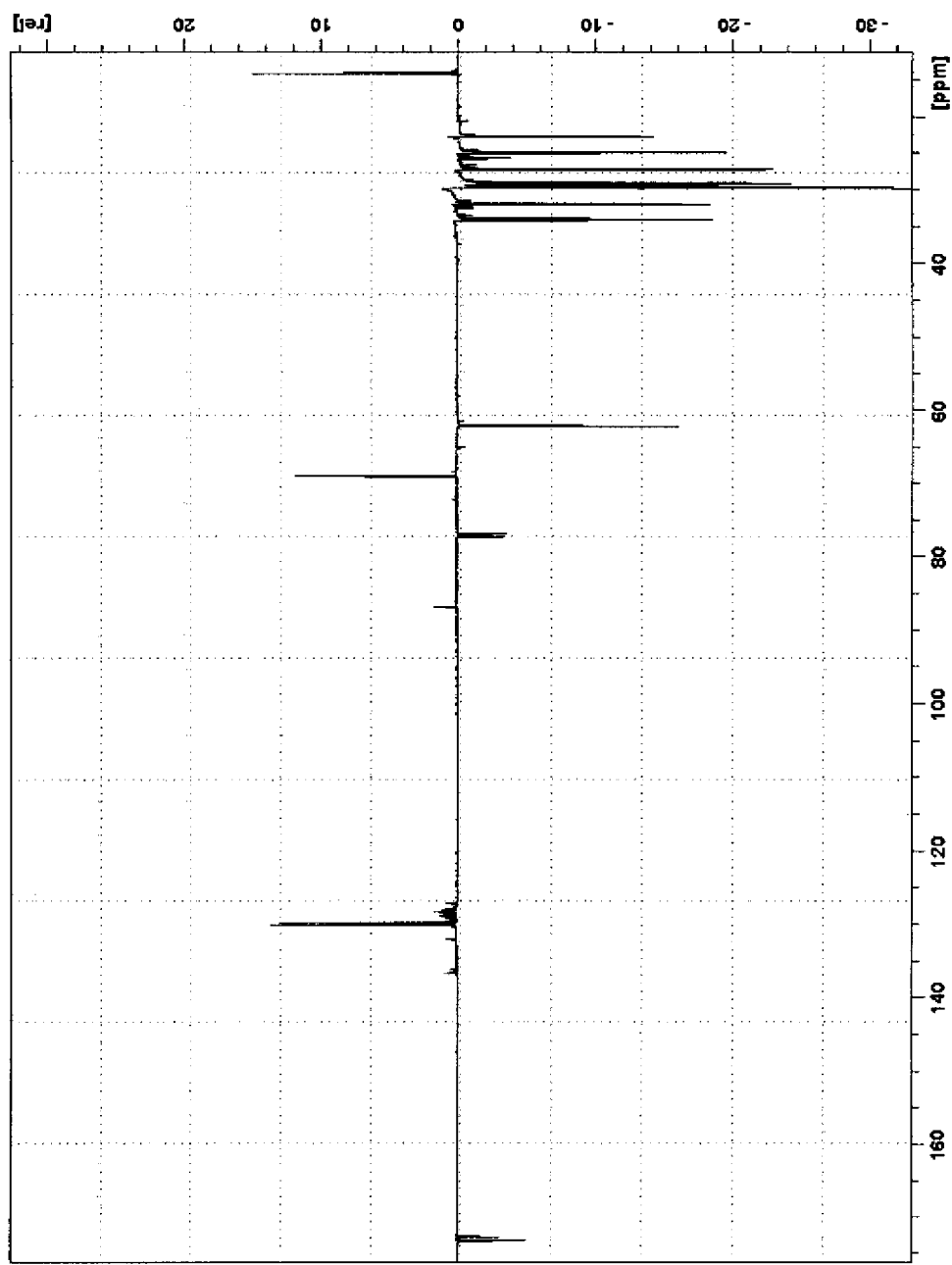
FIG. 3 shows a $^{13}$C NMR spectrum of a sample of extracted lipids.

In order to further demonstrate the suitability of the recovered lipids for use as a fuel or fuel product, the lipid product was also characterized using $^1$H NMR. FIG. 2 shows the $^1$H NMR spectrum for the lipid product (upper spectrum) and for a commercially available canola oil (lower spectrum). As shown in FIG. 2, the recovered lipids are similar in composition to canola oil, including a large proportion of non-polar lipids in the product. FIG. 3 shows a further analysis of the lipid product using $^{13}$C NMR. The $^{13}$C NMR trace shown in FIG. 3 was collected under phase selection of odd or even connected H-atoms. As shown in FIG. 3, the majority of the carbons in the lipid product correspond to carbons in TAG species.

Example 2

Extraction Efficiency of Hot Ethanol

The effectiveness of extraction using hot ethanol was investigated in comparison with a conventional Bligh-Dyer style extraction procedure. Bligh-Dyer type extractions are recognized as a suitable method for extracting a high percentage of available lipids from an algae sample. The following example demonstrates that the use of hot ethanol provided comparable extraction capabilities for extraction of lipids from two different types of algae.

For extraction using hot ethanol, algae cells were lyophilized (or freeze-dried), lysed, and then heated in 95% ethanol for half an hour at 80° C., under sufficient pressure to prevent boiling of the ethanol. The lipids were then recovered by evaporating the ethanol. Similarly lyophilized and lysed cells were also subjected to a Bligh-Dyer extraction. For the Bligh-Dyer extraction, 0.8 volume parts of an aqueous sample of the lyophilized, lysed material was vigorously mixed with 3 parts of a 1:2 (v/v) mixture of chloroform and methanol. This produced a single phase mixture, 1 volume part each of chloroform and water were then added to the single phase with additional mixing, followed by centrifugation of the mixture. The lower chloroform phase containing the lipids was recovered. The lipids were then separated from the chloroform by evaporation.

Two strains of algae (a *Cyclotella* and a *Tetraselmis*) were grown in nitrogen-depleted conditions to induce lipid production. Each type of algae was sampled sufficiently to allow for two comparisons of hot ethanol extraction and Bligh-Dyer extraction, with three replicate samples in each experiment to allow for estimation of experimental variance. The algae samples were also analyzed for lipid yield of whole cultures as fatty acid methyl esters (FAME) in order to establish a baseline for 100% lipid recovery for each algae sample. Table 1 shows the results of the two experiments for lipid recovery from the *Cyclotella* strain using hot ethanol and Bligh-Dyer extractions.

TABLE 1

*Cyclotella* lipid recovery

|  | Experiment 1 | | Experiment 2 | |
| --- | --- | --- | --- | --- |
|  | Bligh-Dyer | 80° C. Ethanol | Bligh-Dyer | 80° C. Ethanoi |
| Recovery (%) | 97.5 | 98.4 | 95.4 | 94.3 |
| Std Dev σ (n = 3) | 0.8 | 1.1 | 1.6 | 3.3 |

In Table 1, Recovery refers to the percentage of lipids recovered in comparison with the whole culture FAME analysis. Std Dev or σ refers to the standard deviation in recovery percentage for the three separate measurements within an experiment. As shown in Table 1, the lipid recovery percentage for 80° C. ethanol is comparable to the recovery percentage for the Bligh-Dyer extraction. Both techniques result in roughly 95% or greater recovery of lipids from an algae sample. This compares favorably to a recovery efficiency of 99-103% on a larger scale extraction determined gravimetrically by weighing the product.

Table 2 shows a similar set of experiments for lipid extraction from a *Tetraselmis* algae strain.

TABLE 2

*Tetraselmis* lipid recovery

|  | Experiment 1 | | Experiment 2 | |
| --- | --- | --- | --- | --- |
|  | Bligh-Dyer | 80° C. Ethanol | Bligh-Dyer | 80° C. Ethanol |
| Recovery (%) | 99.6 | 93.3 | 98.2 | 97.9 |
| Std Dev σ (n = 3) | 1.0 | 3.7 | 1.7 | 4.3 |

Once again both the Bligh-Dyer and 80° C. ethanol extraction techniques result in over 90% recovery of lipids, as compared to the baseline established by whole culture FAME analysis.

Exemplary Embodiments

Production Scale Process Flow

Figure 4:
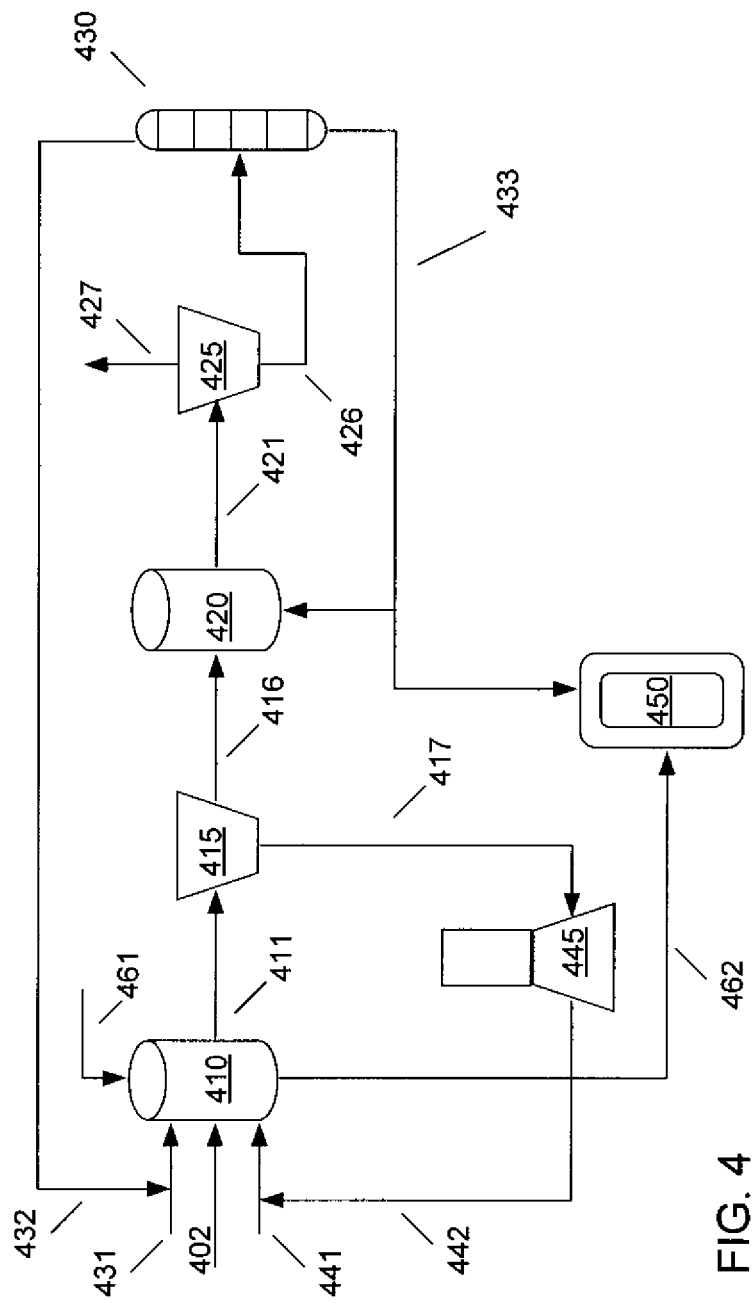
FIG. 4 schematically shows an example of a process flow for product extraction from algae according to an embodiment of the invention.

FIG. 4 schematically shows an example of a process flow suitable for performing solvent extraction of lipids from algae at elevated pressures. In FIG. 4, a reaction vessel 410 is capable of performing a solvent extraction process under effective solvent extraction conditions that include elevated pressures, such as pressures greater than 100 psig (0.7 MPag), or greater than 300 psig (2.1 MPag). Optionally, the reaction vessel 410 can be suitable for performing an extraction at pressures up to about 2500 psig (17.2 MPag). In the embodiment shown in FIG. 4, algae paste 402 and diatomaceous earth 441 are introduced into reaction vessel 410. A portion of the diatomaceous earth 441 can be provided as recycled diatomaceous earth 442. If mixing is desired, the algae paste 402 and diatomaceous earth 441 may be mixed prior to entering vessel 410, or the mixing can occur within the reaction vessel. In the embodiment shown in FIG. 4, an optional water wash may be performed in vessel 410 prior to solvent extraction. During a water wash, fresh water 461 is introduced into vessel 410. This allows for removal of salts entrained in algae paste 402 via aqueous wash effluent 462. If the water wash is performed at an elevated pressure, at least a portion of water soluble proteins and/or carbohydrates may also be included in aqueous wash effluent 462. If desired, at least a portion of the aqueous wash effluent may undergo further processing, such as to purify the wash effluent or to convert the proteins or carbohydrates to another form. The water, the salt, and/or the proteins or carbohydrates can be recycled for another use, such as facilitating additional algae growth in an algae growth environment 450. Alternatively, a wash effluent may be directed, with or without further processing, to a fermenter or an anaerobic digester.

The embodiment shown in FIG. 4 corresponds to a batch or semi-batch type process, where a water wash and solvent extraction occur in a single vessel. As an alternative, the optional water wash can be performed in a separate vessel. The washed algae paste and diatomaceous earth would then be passed into reaction vessel 410 for solvent extraction. This alternate type of configuration could allow for a continuous process.

After the optional water wash, a solvent 431 (such as ethanol) is introduced into reaction vessel 410. A portion of solvent 431 may correspond to recycled solvent 432. The solvent, algae paste, and diatomaceous earth are exposed to effective reaction conditions in the reaction vessel 410 that include elevated temperatures and pressures. After exposure to effective extraction conditions, the contents of the reaction vessel are passed 411 into a separator stage 415. Separator 415 includes at least a solid-liquid separation stage for separating the diatomaceous earth and residual algae solids from the solvent and desired products. At least a portion of the diatomaceous earth and residual algae solids 417 can then be processed 445 to allow for recycle of the diatomaceous earth. The goal of processing 445 is to remove the residual algae solids so that the diatomaceous earth is suitable for mixing again with more algae for processing. One option for regenerating the diatomaceous earth is to perform a digestion process on the residual algae solids in the diatomaceous earth. Another option is to burn off the residual solids, as the silica in the diatomaceous earth will typically not be harmed by a moderate temperature combustion process. The energy derived from a digestion or burning process can be used (via heat exchange) in fractionation processes, as fractionation processes typically will require low level heating for distillations at or below 100° C. The regenerated diatomaceous earth can then be recycled for use in any convenient manner, such as by forming a slurry of the diatomaceous earth that is suitable for flowing through processing equipment or fluidized by an inert gas such as $N_2$.

Separator 415 also generates at least one liquid phase 416. For example, liquid phase 416 can correspond to a mixture of water, the solvent used for the extraction, and products extracted from the algae. The water will typically be present due to either water from the optional water wash or water that was not practical to remove from the algae prior to processing. The products can be concentrated and/or separated out from the water and solvent by any convenient method. In the embodiment shown in FIG. 4, the liquid phase 416 is passed into a vessel 420 where additional water 433 is added. Adding more water to the liquid phase 416 reduces the solubility of the products in the solvent/water mixture, resulting in formation of a product oil phase. In FIG. 4, the mixed phases are passed into a liquid-liquid separator 425 for removal of the product phase as a product stream 427. The other phase generates at least a stream 426 containing water and solvent. Stream 426 can be distilled in a fractionator or distillation column 430 to separate the solvent 432 from water 433. In FIG. 4, solvent 432 recovered from fractionator 430 is shown as being recycled for use in processing additional algae. In addition to using water 433 for the separation process in vessel 420, any excess water is shown as being recycled to an algae growth environment 450.

Figure 5:
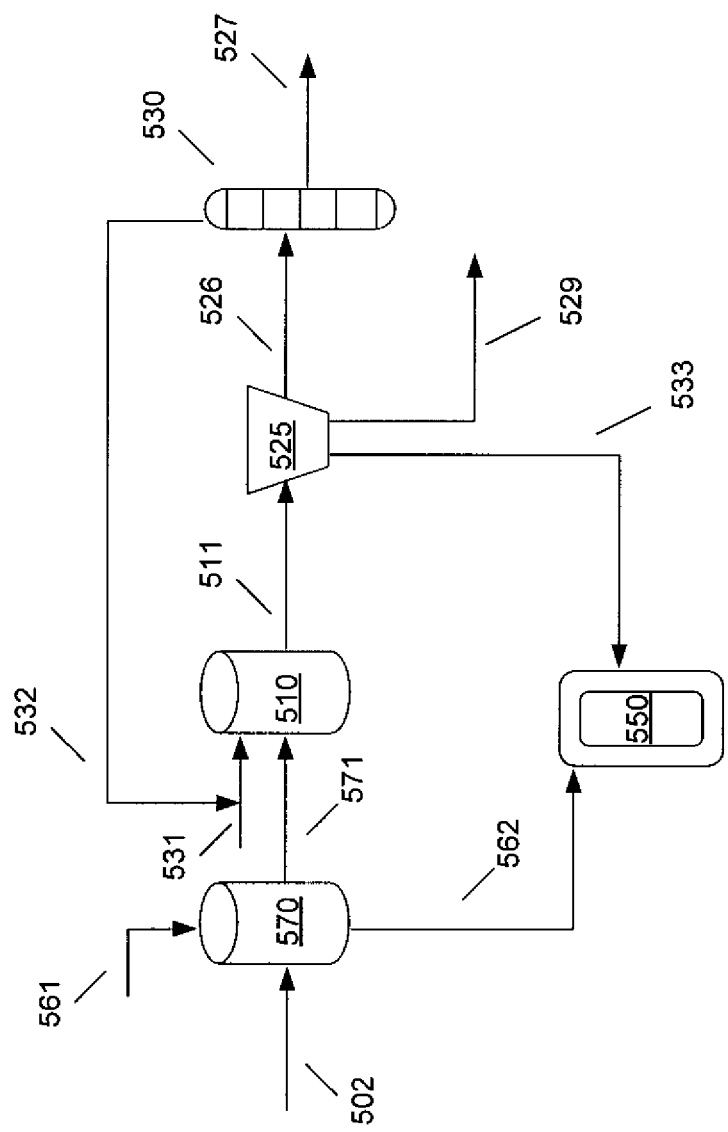
FIG. 5 schematically shows another example of a process flow for product extraction from algae according to an embodiment of the invention.

FIG. 5 shows an example of another type of process flow suitable for performing solvent extraction of lipids or oils from algae at elevated pressures. In the embodiment shown in FIG. 5, the extraction is performed without the presence of the diatomaceous earth or other granular support.

In FIG. 5, an algae paste 502 (or other algae feed containing some water) is passed into a wash vessel 570. In FIG. 5, the optional water wash is performed in a separate wash vessel 570 prior to introducing the algae into reaction vessel 510. Water 561 is passed through wash vessel 570 to remove salts and optionally to remove water soluble proteins and/or carbohydrates. The water wash can be performed at atmospheric pressure, or an elevated pressure can be used. The aqueous effluent 562 can be discarded, or preferably at least a portion of the aqueous effluent can be recycled for further use, such as by recycling the water, salts, proteins, and/or carbohydrates to an algae growth environment 550. Optionally, the aqueous effluent can be subjected to further processes prior to recycling to improve bioavailability of nutrients.

The optionally washed algae paste 571 is then passed into reaction vessel 510 for solvent extraction. A solvent 531 is also introduced into reaction vessel 510. Suitable solvents 531 include alkanes such as n-hexane, methyl tertbutyl ether, isopropanol, butanol, dichloromethane, or ethyl acetate. Optionally, at least a portion of solvent 531 can correspond to recycled solvent 532. The optionally washed algae paste 571 is exposed to the solvent 531 under effective solvent extraction conditions. The mixture of liquids and solids 511 generated by solvent extraction is then passed into a separator 525. Separator 525 can correspond to one or more separation stages for performing desired separations. For example, if an immiscible or only partially miscible solvent is used, the mixture 511 can include at least a solids phase of residual algae solids, an aqueous phase due to water that was present in the algae paste and/or that was introduced during the optional water wash, and a solvent phase that also contains a majority of the desired products.

To separate the different phases present in mixture 511, a separator 525 can include a gravity settling tank to allow for separation into distinct phases. A liquid-liquid separator can then be used to remove the solvent/product phase as a stream 526. The residual algae solids 529 can be separated from the aqueous phase 533 using a solids-liquid separation stage. The residual algae solids can undergo further processing to form additional products. Examples of additional processing include digestion or gasification to form nutrients for additional algae growth, or fermentation of the residual algae solids to generate alcohols or other oxygenates. In FIG. 5, the aqueous phase 533 is shown as being recycled to an algae growth environment 550. This recycling is optional, and can occur after additional processing of the aqueous phase 533. Alternatively, a wash effluent may be directed, with or without further processing, to a fermenter or an anaerobic digester.

To recover the desired product, at least a portion of solvent/product stream 526 is distilled in a fractionator or distillation column 530. The solvent 532 recovered from distillate is shown in FIG. 5 as being recycled for further algae processing. The desired products 527 can also be optionally further processed.

Although the configuration in FIG. 5 is designed for use with an immiscible or partially miscible solvent, separator 525 can be readily adapted for separation of a solvent that is miscible with water, such as ethanol. For example, one or more separators suitable for use as separator 425 in FIG. 4 could be used in place of separator 525. Alternatively, the configuration shown in FIG. 4 could be adapted to perform solvent extraction without the use of diatomaceous earth.

Other Embodiments

Additionally or alternatively, the present invention can include one or more of the following aspects.

Embodiment 1

A method for recovering products from algae, comprising: mixing an algae feed with particulate solids, the algae feed comprising from 0.1 wt % to about 30 wt % algae in water, the particulate solids having an average particle size between about 1 μm and about 200 μm, the weight of the particulate solids being at least about 10% of the weight of the algae feed; exposing the algae feed to a solvent under effective solvent extraction conditions, the effective solvent extraction conditions including a temperature of at least about 40° C. and a pressure of about 100 psig (0.7 MPag) to about 2500 psig (17.2 MPag), to form an extraction mixture comprising the solvent, the particulate solids, water, extracted products, and residual algae solids; and recovering at least a portion of the extracted products from the extraction mixture.

Embodiment 2

The method of embodiment 1, wherein the method further comprises a washing step prior to exposing the algae feed to a solvent, wherein the algae feed is washed with water under effective washing conditions to produce a washed algae feed and a wash effluent.

Embodiment 3

The method of embodiment 2, wherein the effective washing conditions comprise exposing the algae feed to an amount of water corresponding to at least the weight of the algae feed for about 2 minutes to about 15 minutes at a temperature of about 20° C. to about 60° C.

Embodiment 4

The method of embodiment 3, wherein the effective washing conditions further comprise a pressure of about 100 psig (0.7 MPag) to about 300 psig (2.1 MPag), preferably about 300 psig (2.1 MPag) to about 2000 psig (13.8 MPag).

Embodiment 5

The method of any of embodiments 2 to 4, wherein at least a portion of the wash effluent is recycled to an algae growth environment.

Embodiment 6

The method of embodiment 5, wherein recycling at least a portion of the wash effluent comprises: separating metal salts, water-soluble proteins, water-soluble carbohydrates, or a combination thereof from water in the wash effluent; and recycling at least a portion of the separated metal salts, water-soluble proteins, water-soluble carbohydrates, or combination thereof.

Embodiment 7

The method of any of the above embodiments, wherein the particulate solids comprise diatomaceous earth, fine mesh sand, or a combination thereof.

Embodiment 8

The method of any of the above embodiments, wherein the solvent is a water miscible solvent, and/or the solvent comprises ethanol, butanol, an organic alcohol or ketone containing 4 carbons or less, a cyclic ether containing 5 carbons or less, or a combination thereof.

Embodiment 9

The method of any of the above embodiments, wherein the effective solvent extraction conditions comprise a temperature greater than the standard boiling point of the solvent and a pressure greater than a vapor pressure of the solvent at the temperature.

Embodiment 10

The method of any of the above embodiments, wherein the effective solvent extraction conditions comprise a temperature of about 80° C. to about 200° C.

Embodiment 11

The method of embodiment 10, wherein the solvent is methanol, ethanol, propanol, isopropanol, isobutanol, or n-butanol.

Embodiment 12

The method of any of the above embodiments, wherein the effective solvent extraction conditions comprise a pressure of about 100 psig (0.7 MPag) to about 300 psig (2.1 MPag), preferably about 300 psig (2.1 MPag) to about 2000 psig (13.8 MPag).

Embodiment 13

The method of any of the above embodiments, wherein the effective solvent extraction conditions comprise a pressure greater than the vapor pressure of the solvent at the temperature by at least about 50%.

Embodiment 14

The method of any of the above embodiments, wherein recovering at least a portion of the extracted products from the extraction mixture comprises: adding water to the extraction mixture to form an aqueous phase and a non-aqueous phase, the non-aqueous phase comprising at least 50 wt % of the extracted products; and separating the non-aqueous phase from the aqueous phase.

Embodiment 15

The method of any of the above embodiments, wherein recovering at least a portion of the extracted products further comprises recovering at least a portion of the solvent, and wherein the algae feed is exposed to a solvent comprising at least a portion of the recovered solvent.

Embodiment 16

The method of any of the above embodiments, further comprising; recovering at least a portion of the particulate solids and residual algae solids; and regenerating the recovered particulate solids by digesting the residual algae solids, wherein the algae feed is mixed with particulate solids comprising at least a portion of the regenerated, recovered particulate solids.

Embodiment 17

The method of any of the above embodiments, wherein the extracted products comprise fuel products, fuel blending products, products that can be converted to form a fuel product or fuel blending product, or a combination thereof.

Embodiment 18

A method for recovering products from algae, comprising: exposing an algae feed to a solvent under effective solvent extraction conditions, the algae feed comprising from 0.1 wt % to about 30 wt % algae in water, the effective solvent extraction conditions including a temperature of at least about 40° C. and a pressure greater than the vapor pressure of the solvent at the temperature, to form an extraction mixture comprising the solvent, water, extracted products, and residual algae solids; and recovering at least a portion of the extracted products from the extraction mixture.

Embodiment 19

The method of embodiment 18, wherein recovering at least a portion of the extracted products comprises separating the extraction mixture to form a first stream comprising at least 50 wt % of the water and at least 50 wt % of the residual algae solids and a second stream comprising at least 50 wt % of the solvent and at least 50 wt % of the extracted products; and recovering at least a portion of the extracted products from the solvent.

Embodiment 20

The method of any of embodiments 18 to 19, wherein the solvent comprises one or more alkanes, dichloromethane, ethyl acetate, or a combination thereof, or a petroleum stream.

Embodiment 21

The method of any of embodiments 18 to 20, wherein the effective solvent extraction conditions comprise a temperature greater than the standard boiling point of the solvent.

Embodiment 22

The method of any of embodiments 18 to 21, wherein the effective solvent extraction conditions comprise a temperature of about 80° C. to about 200° C.

Embodiment 23

The method of any of embodiments 18 to 22, wherein the effective solvent extraction conditions comprise a pressure from about 300 psig (2.1 MPag) to about 2000 psig (13.8 MPag), preferably from about 500 psig (3.4 MPag) to about 1000 psig (6.9 MPag).

Embodiment 24

The method of any of embodiments 18 to 23, wherein the effective solvent extraction conditions comprise a pressure greater than the vapor pressure of the solvent at the temperature by at least about 50%.

Embodiment 25

The method of any of embodiments 18 to 24, further comprising washing the algae feed with water under effective washing conditions to produce a washed algae feed and a wash effluent, the effective washing conditions comprise exposing the algae feed to an amount of water corresponding to at least the weight of the algae feed for about 2 minutes to about 15 minutes at a temperature of about 20° C. to about 60° C.

Embodiment 26

The method of embodiment 25, wherein the effective washing conditions further comprise a pressure of about 100 psig (0.7 MPag) to about 300 psig (2.1 MPag).

Embodiment 27

The method of any of embodiments 25 to 26, wherein at least a portion of the wash effluent is recycled to an algae growth environment.

Embodiment 28

The method of embodiment 27, wherein recycling at least a portion of the wash effluent comprises: separating metal salts, water-soluble proteins, water-soluble carbohydrates, or a combination thereof from water in the wash effluent; and recycling at least a portion of the separated metal salts, water-soluble proteins, water-soluble carbohydrates, or combination thereof.

Embodiment 29

The method of any of embodiments 18 to 28, wherein the solvent is methanol, ethanol, propanol, isopropanol, isobutanol, or n-butanol.

Embodiment 30

The method of any of embodiments 18 to 29, wherein recovering at least a portion of the extracted products further comprises recovering at least a portion of the solvent, and wherein the algae feed is exposed to a solvent comprising at least a portion of the recovered solvent.

Embodiment 31

A method for recovering products from algae, comprising: washing an algae feed with water under effective washing conditions to produce a washed algae feed and a wash effluent, the algae feed comprising from 0.1 wt % to about 30 wt % algae in water, exposing the washed algae feed to a solvent comprising ethanol under effective solvent extraction conditions, the effective solvent extraction conditions including a temperature of at least about 50° C. and a pressure of about 14 psig (0.1 MPag) to about 200 psig (1.4 MPag), the pressure being greater than a vapor pressure of the ethanol at the temperature, to form an extraction mixture comprising the ethanol, water, extracted non-polar products, and residual algae solids; and recovering at least a portion of the non-polar extracted products from the ethanol.

Embodiment 32

The method of embodiment 31, further comprising mixing the algae feed with particulate solids, the particulate solids having an average particle size between about 1 µm and about 200 µm, the weight of the particulate solids being at least about 10% of the weight of the algae feed.

Embodiment 33

The method of embodiment 32 wherein the particulate solids comprise diatomaceous earth particulate solids, fine mesh sand or a combination thereof.

Embodiment 34

The method of any of embodiments 31 to 33, wherein recovering at least a portion of the non-polar extracted products from the extraction mixture comprises: adding water to the extraction mixture to form an aqueous phase and a non-aqueous phase, the non-aqueous phase comprising at least 50 wt % of the no-polar extracted products; and separating the non-aqueous phase from the aqueous phase.

Embodiment 35

The method of embodiment 34, wherein the effective solvent extraction conditions comprise a temperature of about 50° C. to about 100° C.

Embodiment 36

A method for recovering products from algae, comprising: exposing an algae feed to an aqueous-based solvent under effective solvent extraction conditions, the algae feed comprising from 0.1 wt % to about 30 wt % algae in water, the effective solvent extraction conditions including a temperature of at least about 40° C. and a pressure greater than the vapor pressure of the solvent at the temperature, to form an extraction mixture comprising the aqueous-based solvent, extracted products, and residual algae solids; adding an organic solvent to the extraction mixture; separating the extraction mixture to form a first stream comprising at least 50 wt % of the water and at least 50 wt % of the residual algae solids and a second stream comprising at least 50 wt % of the organic solvent and at least 50 wt % of the extracted products; and recovering at least a portion of the extracted products from the solvent.

Embodiment 37

The method of embodiment 36, wherein the pressure is from about 300 psig (2.1 MPag) to about 2000 psig (13.8 MPag).

Embodiment 38

The method of embodiment 37, wherein the effective solvent extraction conditions comprise a pressure greater than the vapor pressure of the solvent at the temperature by at least about 50%.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

What is claimed is:

1. A method for recovering products from algae, comprising:
    mixing an algae feed with particulate solids, the algae feed comprising from 0.1 wt % to about 30 wt % algae in water, the particulate solids having an average particle size between about 1 μm and about 200 μm, the weight of the particulate solids being at least about 10% of the weight of the algae feed;
    exposing the algae feed to a solvent under effective solvent extraction conditions, the effective solvent extraction conditions including a temperature of at least about 40° C. and a pressure of about 100 psig (0.7 MPag) to about 2500 psig (17.2 MPag), to form an extraction mixture comprising the solvent, the particulate solids, water, extracted products, and residual algae solids; and
    recovering at least a portion of the extracted products from the extraction mixture by separating the extraction mixture to form a first stream comprising at least 50 wt % of the water and at least 50 wt % of the residual algae solids and a second stream comprising at least 50 wt % of the solvent and at least 50 wt % of the extracted products, thereafter recovering at least a portion of the extracted products from the solvent.

2. The method of claim 1, wherein the method further comprises a washing step prior to exposing the algae feed to a solvent, wherein the algae feed is washed with water under effective washing conditions to produce a washed algae feed and a wash effluent.

3. The method of claim 2, wherein the effective washing conditions comprise exposing the algae feed to an amount of water corresponding to at least the dry weight of the algae feed for about 2 minutes to about 15 minutes at a temperature of about 20° C. to about 60° C.

4. The method of claim 3, wherein the effective washing conditions further comprise a pressure of about 100 psig (0.7 MPag) to about 300 psig (2.1 MPag).

5. The method of claim 3, wherein the effective washing conditions further comprise a pressure of about 300 psig (2.1 MPag) to about 2000 psig (13.8 MPag).

6. The method of claim 2, 3, 4 or 5, wherein at least a portion of the wash effluent is recycled to an algae growth environment.

7. The method of claim 6, wherein recycling at least a portion of the wash effluent comprises:
    separating metal salts, water-soluble proteins, water-soluble carbohydrates, or a combination thereof from water in the wash effluent; and
    recycling at least a portion of the separated metal salts, water-soluble proteins, water-soluble carbohydrates, or combination thereof.

8. The method of claim 1, wherein the particulate solids comprise diatomaceous earth, fine mesh sand, or a combination thereof.

9. The method of claim 1, wherein the solvent comprises ethanol, butanol, an organic alcohol or ketone containing 4 carbons or less, a cyclic ether containing 5 carbons or less, or a combination thereof.

10. The method of claim 1, wherein the effective solvent extraction conditions comprise a temperature greater than the standard boiling point of the solvent and a pressure greater than a vapor pressure of the solvent at the temperature.

11. The method of claim 1, wherein the effective solvent extraction conditions comprise a temperature of about 80° C. to about 200° C.

12. The method of claim 11, wherein the solvent is methanol, ethanol, propanol, isopropanol, isobutanol, or n-butanol.

13. The method of claim 1, wherein the effective solvent extraction conditions comprise a pressure of about 100 psig (0.7 MPag) to about 300 psig (2.1 MPag).

14. The method of claim 1, wherein the effective solvent extraction conditions comprise a pressure of about 300 psig (2.1 MPag) to about 2000 psig (13.8 MPag).

15. The method of claim 1, wherein the effective solvent extraction conditions comprise a pressure greater than the vapor pressure of the solvent at the temperature by at least about 50%.

16. The method of claim 1, wherein recovering at least a portion of the extracted products further comprises recovering at least a portion of the solvent, and wherein the algae feed is exposed to a solvent comprising at least a portion of the recovered solvent.

17. The method of claim 1, further comprising:
    recovering at least a portion of the particulate solids and residual algae solids; and
    regenerating the recovered particulate solids by digesting the residual algae solids,
    wherein the algae feed is mixed with particulate solids comprising at least a portion of the regenerated, recovered particulate solids.

18. The method of claim 1, wherein the extracted products comprise fuel products, fuel blending products, products that can be converted to form a fuel product or fuel blending product, or a combination thereof.

19. A method for recovering products from algae, comprising:
    exposing an algae feed to a solvent under effective solvent extraction conditions, the algae feed comprising from 0.1 wt % to about 30 wt % algae in water, the effective solvent extraction conditions including a temperature of at least about 40° C. and a pressure greater than the vapor pressure of the solvent at the temperature, to form an extraction mixture comprising the solvent, water, extracted products, and residual algae solids; and recovering at least a portion of the extracted products from the extraction mixture by separating the extraction mixture to form a first stream comprising at least 50 wt % of the water and at least 50 wt % of the residual algae solids and a second stream comprising at least 50 wt % of the solvent and at least 50 wt % of the extracted products, thereafter recovering at least a portion of the extracted products from the solvent.

20. The method of claim 19, wherein the solvent comprises one or more alkanes, dichloromethane, ethyl acetate, or a combination thereof.

21. The method of claim 19, wherein the solvent comprises a petroleum stream.

22. The method of claim 19, wherein the effective solvent extraction conditions comprise a temperature greater than the standard boiling point of the solvent.

23. The method of claim 19, wherein the effective solvent extraction conditions comprise a temperature of about 80° C. to about 200° C.

24. The method of claim 19, wherein the effective solvent extraction conditions comprise a pressure from about 300 psig (2.1 MPag) to about 2000 psig (13.8 MPag).

25. The method of claim 19, wherein the effective solvent extraction conditions comprise a pressure of about 500 psig (3.4 MPag) to about 1000 psig (6.9 MPag).

26. The method of claim 19, wherein the effective solvent extraction conditions comprise a pressure greater than the vapor pressure of the solvent at the temperature by at least about 50%.

27. The method of claim 19, further comprising washing the algae feed with water under effective washing conditions to produce a washed algae feed and a wash effluent, the effective washing conditions comprise exposing the algae feed to an amount of water corresponding to at least the weight of the algae feed for about 2 minutes to about 15 minutes at a temperature of about 20° C. to about 60° C.

28. The method of claim 27, wherein the effective washing conditions further comprise a pressure of about 100 psig (0.7 MPag) to about 300 psig (2.1 MPag).

29. The method of claim 27, wherein at least a portion of the wash effluent is recycled to an algae growth environment.

30. The method of claim 29, wherein recycling at least a portion of the wash effluent comprises:

separating metal salts, water-soluble proteins, water-soluble carbohydrates, or a combination thereof from water in the wash effluent; and recycling at least a portion of the separated metal salts, water-soluble proteins, water-soluble carbohydrates, or combination thereof.

31. The method of claim 19, wherein the solvent is methanol, ethanol, propanol, isopropanol, isobutanol, or n-butanol.

32. The method of claim 19, wherein recovering at least a portion of the extracted products further comprises recovering at least a portion of the solvent, and wherein the algae feed is exposed to a solvent comprising at least a portion of the recovered solvent.

33. A method for recovering products from algae, comprising:

washing an algae feed with water under effective washing conditions to produce a washed algae feed and a wash effluent, the algae feed comprising from 0.1 wt % to about 30 wt % algae in water;

exposing the washed algae feed to a solvent comprising ethanol under effective solvent extraction conditions, the effective solvent extraction conditions including a temperature of at least about 50° C. and a pressure of about 14 psig (0.1 MPag) to about 200 psig (1.4 MPag), the pressure being greater than a vapor pressure of the ethanol at the temperature, to form an extraction mixture comprising the ethanol, water, extracted non-polar products, and residual algae solids; and recovering at least a portion of the non-polar extracted products from the ethanol by separating the extraction mixture to form a first stream comprising at least 50 wt % of the water and at least 50 wt % of the residual algae solids and a second stream comprising at least 50 wt % of the ethanol and at least 50 wt % of the extracted non-polar products, thereafter recovering at least a portion of the extracted non-polar products from the ethanol.

34. The method of claim 33, further comprising mixing the algae feed with particulate solids, the particulate solids having an average particle size between about 1 μm and about 200 μm, the weight of the particulate solids being at least about 10% of the dry weight of the algae feed.

35. The method of claim 34, wherein the particulate solids comprise diatomaceous earth particulate solids, fine mesh sand, or a combination thereof.

* * * * *